US008827124B2

(12) United States Patent
Painchaud et al.

(10) Patent No.: US 8,827,124 B2
(45) Date of Patent: Sep. 9, 2014

(54) LIQUID DISPENSING DEVICE

(75) Inventors: Gaetan Painchaud, Francheville (FR); Guillaume Grevin, L'Isle d'Abeau (FR); Thierry Decock, Paris (FR); Xavier Julia, Villefontaine (FR)

(73) Assignee: Rexam Healthcare la Verpilliere (FR)

( * ) Notice: Subject to any disclaimer, the term of this patent is extended or adjusted under 35 U.S.C. 154(b) by 0 days.

(21) Appl. No.: 13/418,146

(22) Filed: Mar. 12, 2012

(65) Prior Publication Data
US 2012/0305599 A1 Dec. 6, 2012

Related U.S. Application Data

(63) Continuation of application No. PCT/FR2010/051878, filed on Sep. 9, 2010.

(30) Foreign Application Priority Data

Sep. 11, 2009 (FR) ..................................... 09 56279

(51) Int. Cl.
*B67D 3/00* (2006.01)
(52) U.S. Cl.
USPC ....... 222/547; 222/212; 222/189.06; 222/422
(58) Field of Classification Search
USPC .......... 222/547, 560, 561, 422, 525, 397, 95, 222/105, 387, 401.1, 402.14, 402.22, 222/402.25, 380, 511–522, 477, 482, 222/189.06, 189.09, 212–215, 206, 491; 239/571, 575; 128/205.13, 205.11
See application file for complete search history.

(56) References Cited

U.S. PATENT DOCUMENTS

| | | | | |
|---|---|---|---|---|
| 1,759,081 A * | 5/1930 | Anderson | ....................... | 137/331 |
| 2,759,643 A * | 8/1956 | Dahlin | ......................... | 222/521 |
| 5,154,325 A * | 10/1992 | Ryder et al. | ............. | 222/189.06 |
| 5,370,313 A | 12/1994 | Beard | | |
| 5,605,257 A * | 2/1997 | Beard | ....................... | 222/189.09 |
| 5,676,289 A * | 10/1997 | Gross et al. | ................... | 222/494 |
| 7,637,402 B2 * | 12/2009 | Romanov et al. | ............. | 222/547 |
| 7,950,391 B2 * | 5/2011 | Fuchs | ....................... | 128/205.13 |
| 2004/0187935 A1 * | 9/2004 | Arzenton et al. | ........ | 137/614.04 |
| 2004/0245290 A1 * | 12/2004 | Hagihara | ....................... | 222/207 |
| 2005/0258282 A1 * | 11/2005 | Hagihara | ....................... | 239/571 |
| 2007/0113841 A1 | 5/2007 | Fuchs | | |
| 2007/0210115 A1 | 9/2007 | Stadelhofer et al. | | |

* cited by examiner

FOREIGN PATENT DOCUMENTS

| | | |
|---|---|---|
| EP | 1520797 A1 | 4/2005 |
| JP | H09507412 A | 7/1997 |
| WO | 9518681 A1 | 7/1995 |
| WO | 2004069679 A1 | 8/2004 |

OTHER PUBLICATIONS

International Search Report; Application No. PCT/FR2010/051878; Issued: Jan. 27, 2011; Mailing Date: Feb. 3, 2011; 2 pages.

*Primary Examiner* — Frederick C Nicolas
*Assistant Examiner* — Bob Zadeh
(74) *Attorney, Agent, or Firm* — St. Onge Steward Johnston & Reens LLC

(57) ABSTRACT

A liquid dispenser device including a container for storing the liquid to be dispensed, a dispenser endpiece mounted on the container, being provided with a support and a liquid dispenser valve, the valve including an elastomer material and being capable of taking up a blocking configuration and a liquid-passing configuration by co-operating with the support, and a flowrate-reducer member including a liquid-deflector shape defining a flowrate-reducer channel, the flowrate-reducer member being a part that is separate from the support and separate from the valve.

14 Claims, 1 Drawing Sheet

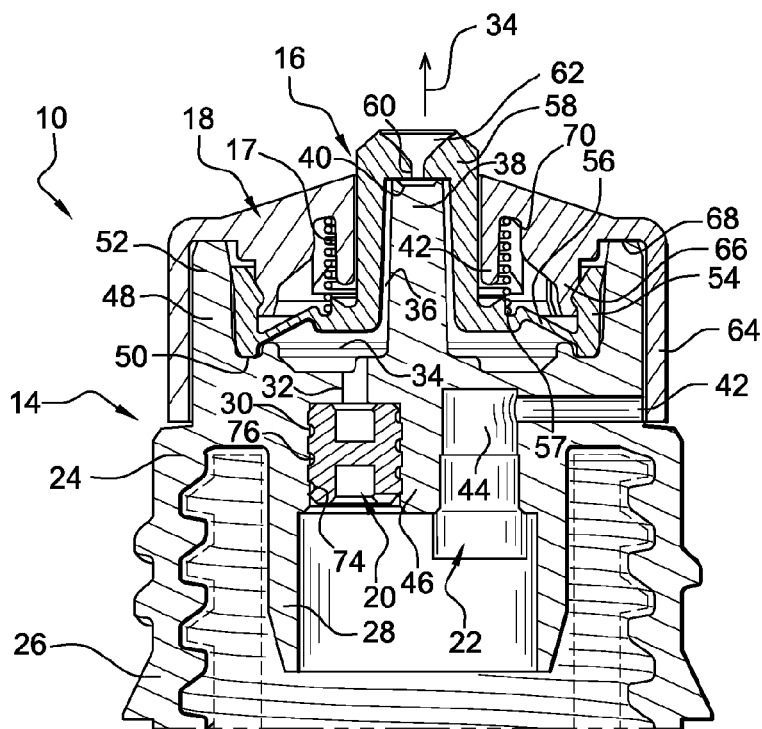
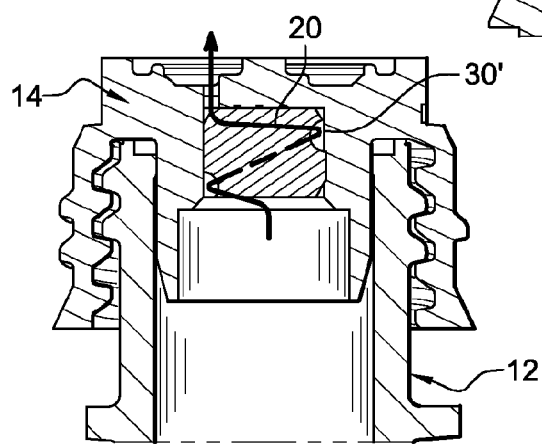
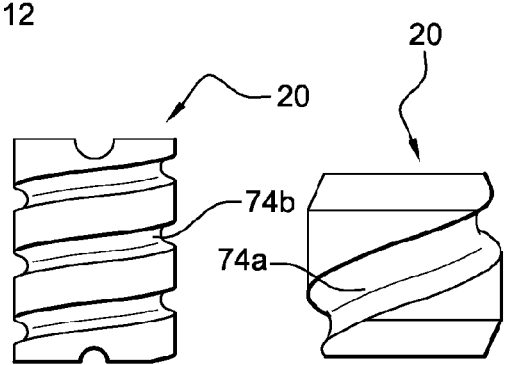
Fig. 1
Fig. 2
Fig. 3b
Fig. 3a
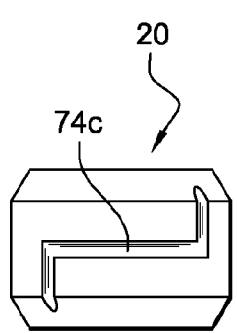
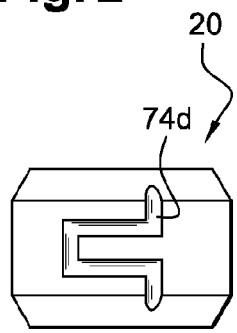
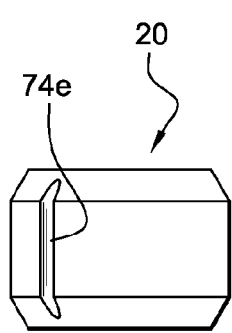
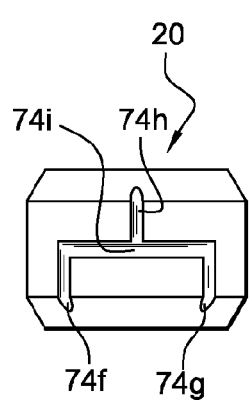
Fig. 3c
Fig. 3d
Fig. 3e
Fig. 3f

LIQUID DISPENSING DEVICE

CROSS-REFERENCE TO RELATED APPLICATIONS

The present application is a continuation of pending International patent application PCT/FR2010/051878 filed on Sep. 9, 2010 which designates the United States and claims priority from French patent application 0956279 filed on Sep. 11, 2009, the content of which is incorporated herein by reference.

FIELD OF THE INVENTION

The invention relates to the field of dispensing liquid, in particular in the form of drops in the pharmaceutical field, e.g. liquid for eyedrops or for eardrops.

BACKGROUND OF THE INVENTION

Liquid dispenser devices are already known that are provided with a container and a dispenser endpiece mounted on the container, the endpiece being provided with a support and with a closure element. For example, in document US 2007/0210115, the dispenser endpiece comprises a support having a closure element movable inside it between a blocking configuration and a liquid-passing configuration. The closure element also includes, at its distal end in the immediate vicinity of the liquid release orifice, a shape for reducing the flow rate of the liquid. That flowrate-reducer shape comprises a channel of helical shape, of small section, and suitable for deflecting the liquid to generate head loss when a user squeezes the container. By means of this flowrate-reducer shape, it is ensured that the liquid is not dispensed in the form of jets.

The inventors of the present invention have observed that a difficulty lies in the fact that the shape for reducing the flow rate of the liquid is made in the same part as the shape that serves to block or pass the liquid. Such a configuration requires the valve and the support to present dimensions that are very accurate, since it is necessary both to allow the valve to move relative to the support so as to enable the liquid to pass, while also enabling co-operation between the deflector shape and the support that is sufficiently close to obtain a deflector channel that does not leak, since if it did, the flowrate-reducer effect would not occur. Unfortunately, it is difficult to make parts that require such dimensional accuracy.

SUMMARY OF THE INVENTION

A particular object of the present invention is to propose a dispenser device that ensures that the flow rate of the liquid is reduced while guaranteeing satisfactory operation when dispensing liquid.

To this end, the invention provides in particular a liquid dispenser device comprising:
 a container for storing the liquid to be dispensed;
 a dispenser endpiece mounted on the container, being provided with a support and a liquid dispenser valve, the valve comprising an elastomer material and being capable of taking up a blocking configuration and a liquid-passing configuration by co-operating with the support; and
 a flowrate-reducer member comprising a liquid-deflector shape defining a flowrate-reducer channel, the flowrate-reducer member being a part that is separate from the support and separate from the valve.

The flowrate-reducer function is thus performed by means of a third part that is distinct from the valve and the support, i.e. that is separable from the valve and the support, or that is at least separate from both of them before the device is assembled. By making use of a separate part for limiting the flow rate of the liquid, a separation is provided between those portions of the endpiece that provide the device with sealing by blocking or passing the liquid, and those portions that reduce the flow rate. Since flow-rate reduction is performed by a third part that is not located in the direct vicinity of the sealing obtained by co-operation between the valve and the support, the sealing function may be provided independently of the flowrate-reducer function. Thus, each function is performed in optimum and reliable manner. Although it might have been expected that the device would then be more complicated to assemble, since there is an additional fitted part, assembly is in fact simplified because the flowrate-reducer zone is no longer dependent on the shape of the valve and of the support providing the device with sealing. Consequently, it is easier to modify the length or the diameter of said flowrate-reducer shape. In addition, because flowrate-reduction is not provided in the sealing zone of the endpiece, the sealing zone may be shorter, thereby enabling endpieces to be made that are more compact.

Since the functions are separated, fabrication is made easier, given that variations in the dimensions of the parts have less effect on the operation of the device. This is advantageous since, when using precision levels that are too great, industrial difficulties arise such as tools being fragile or molds being broken.

Furthermore, a particular advantage lies in the fact that it is easy to adapt the device as a function of the type of liquid that is to be dispensed. Depending on the viscosity of the liquid, the flowrate-reducer channel needs to present a particular configuration. For example, a flowrate-reducer channel may be provided of greater diameter for liquids that are very viscous. Since the flowrate-reducer member is a separate part, in order to adapt the dispenser endpiece as a function of the type of liquid that is to be dispensed, it then suffices merely to modify the shape of the flowrate-reducer member, without any need also to modify the shape of the valve or the support which may therefore be of standard shape. In addition, since the flow-rate reduction is provided by a separate part, it is possible to provide both devices that present the flowrate-diminishing function and devices that do not, with the only difference between the devices being the presence or the absence of the flowrate-reducer member.

It should be observed that adapting the device as a function of the viscosity of the liquid is particularly advantageous since liquids such as those used for eyedrops are becoming more and more viscous, in particular when they do not include a preservative agent.

The term "flowrate-reducer" is used to mean that the flow speed of the liquid is reduced for given pressure applied on the container by the user. This flow-rate reduction is preferably generated by a channel having a section that is smaller than the other flow channels provided in the device and/or extending over a greater length and/or having an axis that extends transversely.

Advantage may advantageously be taken of the flowrate-reducer member to fill a space in the device, and thus reduce a dead volume situated in the dispenser endpiece, where such a dead volume can lead to bacteria developing.

The dispenser device may also include one or more of the following characteristics.

The support includes a housing for receiving the flowrate-reducer member and co-operating therewith to define the flowrate-reducer channel. By way of example, this housing may be located opposite from the support portion that provides the device with sealing, so as to further limit interactions between flow-rate limitation and sealing. Preferably, this reception housing is substantially cylindrical in shape, defining a cavity of volume that is substantially complementary to the volume of the flowrate-reducer member.

The flowrate-reducer member is substantially cylindrical in shape, the liquid-deflector shape being made in the outer periphery of the flowrate-reducer member and comprising a helical groove. This helical shape of the channel provides a transverse flow direction that is not parallel to the liquid-injection direction, while also providing a relatively long length of channel, thereby enabling head loss to be obtained while occupying a minimum amount of space in the device.

The flowrate-reducer member is substantially cylindrical in shape, the liquid-deflector shape being made in the outer periphery of the flowrate-reducer member and comprising a groove defining angular portions. These angular portions serve to define a path with sharp changes of direction, thereby disturbing fluid flow and giving rise to greater head losses.

The flowrate-reducer member is substantially cylindrical in shape, the liquid-deflector shape being made in the outer periphery of the flowrate-reducer member and comprising a rectilinear groove, preferably substantially parallel to the cylinder axis of the flowrate-reducer member. Because of the geometrical characteristics of the groove, in particular the dimensions of its section, fluid flow is disturbed and gives rise to head losses that may be sufficient to reduce the flow rate.

The flowrate-reducer member is substantially cylindrical in shape, the liquid-deflector shape being made in the outer periphery of the flowrate-reducer member and comprising a network of a plurality of grooves including at least one node where grooves meet. The fluid flows in the various grooves meet at the node. This creates a zone of turbulence that gives rise to high levels of head loss.

The support includes a sealing portion carrying a bearing surface of the valve for blocking the passage of liquid in the blocking configuration, the sealing portion being substantially cylindrical in shape and the bearing surface being placed at the distal end of said cylindrical shape. This sealing portion is substantially in the form of a peg for closing an orifice formed in a corresponding sealing portion of the valve.

The valve includes a substantially cylindrical portion covering the cylindrical shape and co-operating with the cylindrical shape to define a liquid-passing channel arranged downstream from the flowrate-reducer channel.

The valve includes a fastener portion for fastening the valve permanently on the support, and a portion that is substantially in the form of a disk, from which the cylindrical portion projects.

The valve comprises an elastomer material, possibly together with a rigid portion, e.g. serving as a bearing point for a return spring urging the valve into its liquid-blocking position.

The support also includes an air-passing channel for passing air into the container and fitted with a hydrophobic filter.

As can be observed, the support may contribute to several functions in the endpiece, in particular the sealing function, the flowrate-reduction function, the valve fastening function, and/or the function of passing air to ventilate the container.

The invention also provides a batch of two devices as presented above, the two devices presenting respective valves and supports of the same shape and flowrate-reducer members of different shapes. For example, the flowrate-reducer channel may be of a different section, a different length, or indeed a different shape.

BRIEF DESCRIPTION OF THE DRAWINGS

The invention can be better understood on reading the following description given purely by way of example and made with reference to the accompanying drawing, in which:

FIG. 1 is a longitudinal section view of a dispenser device in one embodiment;

FIG. 2 is a fragmentary longitudinal section view of a dispenser device in a second embodiment; and FIGS. 3a to 3f are side views of different variant flowrate-reducer members.

DETAILED DESCRIPTION OF THE INVENTION

FIG. 1 shows a dispenser 10 for dispensing a liquid in the form of drops, for screw-mounting on the neck of a container 12 drawn in dashed lines. The container 12 is a container for storing pharmaceutical liquid, such as a liquid for eyedrops or eardrops. The liquid is dispensed by a user squeezing the body of the container 12, which container may present a certain amount of elasticity so as to return to its initial shape after the user has stopped squeezing.

The dispenser endpiece 10 in this example comprises a support 14, a dispenser valve 16, a spring 17, a cap 18, a flowrate-reducer member 20, and a hydrophobic filter 22.

The valve 16, the support 14, and the flowrate-reducer member 20 constitute distinct parts, i.e. they are fitted to one another, i.e. they are separate before being assembled together.

In this example, the support 14 comprises a fastener portion 24 for fastening on the container, located at the proximal end of the support 14. This portion 24 comprises an outer skirt 26 that is tapped so as to be screwed onto the neck of the container 12. The fastener portion 24 further comprises an inner skirt 26 of tubular shape serving to provide sealing between the container 12 and the dispenser endpiece 10.

The support 14 also includes a housing 30 for receiving the flowrate-reducer member 20, defining a cavity that is substantially cylindrical, said cavity opening out at its proximal end to the container 12 and at its distal end to a first liquid-passing channel 32 arranged in the support 14 and extending it the longitudinal direction of the device, here corresponding to the liquid-ejection direction as represented by arrow 34. This first channel 32 opens out to an intermediate cavity 34, itself opening out to a second liquid-passing channel 36.

The support 14 also includes a central sealing portion 38 of substantially cylindrical shape that extends in the distal direction away from the inner skirt 28. At its distal end, the portion 38 carries a bearing surface 40 of the valve 16 to block the passage of liquid in a blocking configuration. In this example, the bearing surface 40 is in the form of an annular bead.

In this example, the support 14 also includes an air-passing channel 42 for passing air into the container 12, this channel opening out to a housing 44 in which there is received a hydrophobic filter 22. The housing 44 is juxtaposed to the housing 30 for receiving the flowrate-reducer member 20, being separated therefrom by a central wall 46 that extends away from the sealing portion 38.

Finally, the support 14 includes a fastener portion 48 for fastening the valve 16 to the support 14. This portion 48 also acts as a fastener portion for fastening the cap 18 on the support 14. It includes an annular groove 50 defined at its periphery by an annular wall 52. The annular groove 50 is also defined, at its inner periphery, by an annular rib made on a wall that is substantially in the shape of a disk pierced by the channel 32, and defining the cavity 34.

The valve 16 may occupy a blocking configuration and a liquid-passing configuration by co-operating with the support 14. In this example, it is made of an elastomer material. In another example, only a portion of the valve 16 is made of an elastomer material, the remainder being made of a material that is more rigid, suitable for acting as a bearing surface for the spring 17. The valve 16 includes a fastener portion 54 for fastening it to the support 14 and forming a skirt of substantially tubular shape. This fastener portion 54 is connected to a web 56 substantially in the form of a disk and from which a substantially cylindrical central portion 58 projects. The web 56 also includes a bearing seat 57 for the spring 17. The portion 58 defines an inner cavity of substantially cylindrical shape that is complementary to the peg 38. The peg 38 and the cylindrical portion 58 are coaxial and together they define the liquid-passing channel 36. This channel 36 opens out to an outlet channel 60 made in the distal end of the valve 16, in turn opening out into a shape 62 for forming drops.

The cap 18 has an annular fastener portion 64 for fastening to the support 14 and another annular portion 66 coaxial with the portion 64 so as to define a groove 68 in which the annular wall 52 is received. The cap 18 also includes a bearing seat 70 for the spring 17, extended at its inner periphery by an annular wall 72 with the portion 58 passing therethrough and serving to center the portion 58 of the valve 16.

The flowrate-reducer member 20 comprises a liquid-deflector shape 74 co-operating with the housing 30 to define a flowrate-reducer channel 76.

The flowrate-reducer member 20 may take a variety of shapes as shown by way of example in FIGS. 3a to 3f. It is substantially cylindrical in shape, and the deflector shape 74 is formed in its outer periphery, forming a peripheral recess.

In the examples of FIGS. 3a and 3b the shape 74 is defined by a helical groove 74a, 74b that goes around the cylinder 20, preferably through a plurality of turns if the liquid is not very viscous. The groove 74a is of section greater than the groove 74b and it is suitable for liquids of greater viscosity than the groove 74b.

The members 20 in FIGS. 3c and 3d show other types of groove 74c and 74d that do not form a turn around the cylindrical portion of the member 20 and that define angular portions, here right-angled portions, having the effect of decreasing the pressure of the liquid flowing therethrough. Optionally, the member 20 may include, in other portions of its peripheral wall, grooves similar to the grooves 74c and 74d, thereby increasing the liquid flow rate.

The member 20 of FIG. 3e shows a rectilinear groove 74e that is substantially parallel to the axis of the cylindrical portion. In a variant, the member 20 has a plurality of grooves 74e distributed over the entire peripheral wall of the member 20. In another variant, the groove(s) 74e is/are inclined relative to the axis of the cylinder.

The member 20 of FIG. 3f shows a network of grooves 74f-h including a node 74i where the grooves 74f-h meet. The network has upstream grooves 74f-g situated upstream from the node 74i, and at least one downstream groove 74h situated downstream from the node 74i. In a variant, the network has more than two upstream grooves 74f-g, more than one downstream groove 74h, and more than one node 74i.

The operation of the FIG. 1 device is described below.

At rest, i.e. when the user is not squeezing the container 12, the valve 16 is in its liquid-blocking configuration, i.e. it bears against the surface 40 because of the way it is permanently fastened on the support 14 so as to exert resilient stress on the valve under the effect of the pressure delivered by the spring 17.

When a user squeezes the container 12, pressure is exerted on the fluid which flows along the only channel available for it to flow (the hydrophobic filter 22 preventing the liquid from escaping), i.e. via the flowrate-reducer channel 76. As it passes along this channel 76, the flow rate of the fluid is diminished by the head-loss effect. Thereafter this fluid flows along the channel 32, then in the cavity 34 and along the channel 36. Under the effect of the pressure, the fluid lifts the diaphragm 16, which thus passes into its liquid-passing configuration so that liquid can flow between the diaphragm 16 and the bearing surface 40, in order to pass into the channel 60 and into the cavity 61 and thus be presented in the form of a drop.

It should be observed that since the flowrate-reducer member 20 is a separate part, it may be of a shape that varies as a function of the liquid contained in the container. Thus, the housing 30 is adapted to receive members 20 of different shapes, such as the shapes shown in FIGS. 3a to 3f. It is thus possible to fabricate batches comprising endpieces all having the same valves 16, the same supports 14, and the same caps 18, but presenting different members 20.

The endpiece 10 may have configurations other than that shown in FIG. 1, e.g. the configuration shown in FIG. 2.

The endpiece of FIG. 2 functions analogously to the endpiece of FIG. 1, apart from the fact that it does not have an air-passing channel 42. In this embodiment, the container 12 is preferably a container that is deformable in non-elastic manner so there is no need to pass any air in order to compensate for the suction generated by the user on releasing the container after squeezing it. Thus, in this example, the housing 30 is located in the center of the support 14, and the flowrate-reducer member 20 may be of greater diameter.

It should be observed that the invention is not limited to the above-described embodiments.

What is claimed is:

1. A liquid dispenser device comprising:
    a container for storing the liquid to be dispensed;
    a dispenser endpiece mounted on the container, being provided with a support and a liquid dispenser valve, the valve comprising an elastomer material and being capable of taking up a blocking configuration and a liquid-passing configuration by cooperating with the support; and
    a flowrate-reducer member comprising a liquid-deflector shape defining a flowrate-reducer channel, the flowrate-reducer member being a part that is separate from the support and separate from the valve;
    the support having a sealing portion with a bearing surface for blocking the passage of liquid in the blocking configuration, the sealing portion having a cylindrical shape and the bearing surface being disposed at a distal end of the sealing portion, and wherein the valve further includes a cylindrical portion covering the cylindrical shape of the sealing portion and cooperating with the cylindrical shape of the sealing portion to define a cylindrical channel there between and downstream from the flowrate-reducer member;
    wherein the flowrate-reducer member is cylindrical in shape, the liquid-deflector shape being made in an outer perihery of the flowrate-reducer member and comprising a helical groove.

2. The device according to claim 1, wherein the support includes a housing for receiving the flowrate-reducer member and co-operating therewith to define the flowrate-reducer channel.

3. The device according to claim 1, wherein the support also includes an air-passing channel for passing air into the container and fitted with a hydrophobic filter.

4. The device according to claim 1, wherein the flow-rate reducer member is replaceable by a second flow-rate reducer member, the second flow-rate reducer member having a different shape than the flow-rate reducer member.

5. A liquid dispenser device comprising:
a container for storing the liquid to be dispensed;
a dispenser endpiece mounted on the container, being provided with a support and a liquid dispenser valve, the valve comprising an elastomer material and being capable of taking up a blocking configuration and a liquid-passing configuration by cooperating with the support; and
a flowrate-reducer member comprising a liquid-deflector shape defining a flowrate-reducer channel, the flowrate-reducer member being a part that is separate from the support and separate from the valve;
the support having a sealing portion with a bearing surface for blocking the passage of liquid in the blocking configuration, the sealing portion having a cylindrical shape and the bearing surface being disposed at a distal end of the sealing portion, and wherein the valve further includes a cylindrical portion covering the cylindrical shape of the sealing portion and cooperating with the cylindrical shape of the sealing portion to define a cylindrical channel there between and downstream from the flowrate-reducer member;
wherein the flowrate-reducer member is cylindrical in shape, the liquid-deflector shape being made in an outer periphery of the flowrate-reducer member and comprising a groove defining angular portions.

6. The device according to claim 5, wherein the support includes a housing for receiving the flowrate-reducer member and co-operating therewith to define the flowrate-reducer channel.

7. The device according to claim 5, wherein the support also includes an air-passing channel for passing air into the container and fitted with a hydrophobic filter.

8. A liquid dispenser device comprising:
a container for storing the liquid to be dispensed;
a dispenser endpiece mounted on the container, being provided with a support and a liquid dispenser valve, the valve comprising an elastomer material and being capable of taking up a blocking configuration and a liquid-passing configuration by cooperating with the support; and
a flowrate-reducer member comprising a liquid-deflector shape defining a flowrate-reducer channel, the flowrate-reducer member being art that is separate from the support and separate from the valve;
the support having a sealing portion with a bearing surface for blocking the passage of liquid in the blocking configuration, the sealing portion having a cylindrical shape and the bearing surface being disposed at a distal end of the sealing portion, and wherein the valve further includes a cylindrical portion covering the cylindrical shape of the sealing portion and cooperating with the cylindrical shape of the sealing portion to define a cylindrical channel there between and downstream from the flowrate-reducer member;
wherein the flowrate-reducer member is cylindrical in shape, the liquid-deflector shape being made in an outer periphery of the flowrate-reducer member and comprising a rectilinear groove.

9. The device according to claim 8, wherein the rectilinear grove is parallel to a cylinder axis of the flowrate-reducer member.

10. The device according to claim 8, wherein the support includes a housing for receiving the flowrate-reducer member and co-operating therewith to define the flowrate-reducer channel.

11. The device according to claim 8, wherein the support also includes an air-passing channel for passing air into the container and fitted with a hydrophobic filter.

12. A liquid dispenser device comprising:
a container for storing the liquid to be dispensed;
a dispenser endpiece mounted on the container, being provided with a support and a liquid dispenser valve, the valve comsrising an elastomer material and being capable of taking up a blocking configuration and a liquid-passing configuration by cooperating with the support; and
a flowrate-reducer member comprising a liquid-deflector shape defining a flowrate-reducer channel, the flowrate-reducer member being a part that is separate from the support and separate from the valve;
the support having a sealing portion with a bearing surface for blocking the passage of liquid in the blocking configuration, the sealing portion having a cylindrical shape and the bearing surface being disposed at a distal end of the sealing portion, and wherein the valve further includes a cylindrical portion covering the cylindrical shape of the sealing portion and cooperating with the cylindrical shape of the sealing portion to define a cylindrical channel there between and downstream from the flowrate-reducer member;
wherein the flowrate-reducer member is cylindrical in shape, the liquid-deflector shape being made in an outer periphery of the flowrate-reducer member and comprising a network of a plurality of grooves including at least one node where the grooves meet.

13. The device according to claim 12, wherein the support includes a housing for receiving the flowrate-reducer member and co-operating therewith to define the flowrate-reducer channel.

14. The device according to claim 12, wherein the support also includes an air-passing channel for passing air into the container and fitted with a hydrophobic filter.

* * * * *